United States Patent [19]
Andersson

[11] Patent Number: 5,782,885
[45] Date of Patent: Jul. 21, 1998

[54] RATE RESPONSIVE HEART STIMULATION DEVICE USING NEURAL NETWORK AND IEGM CLASSIFIER

[75] Inventor: Jonas Andersson, Johanneshov, Sweden

[73] Assignee: Pacesetter AB, Solna, Sweden

[21] Appl. No.: 797,422

[22] Filed: Feb. 10, 1997

[30] Foreign Application Priority Data

Feb. 12, 1996 [SE] Sweden .................................. 9600512

[51] Int. Cl.$^6$ .................................................. A61N 1/362
[52] U.S. Cl. .................................................. 607/17; 607/9
[58] Field of Search .................................. 607/9, 11, 17, 607/25; 600/523, 525

[56] References Cited

U.S. PATENT DOCUMENTS

| | | |
|---|---|---|
| 5,000,189 | 3/1991 | Throne et al. . |
| 5,203,326 | 4/1993 | Collins . |
| 5,215,098 | 6/1993 | Steinhaus et al. . |
| 5,280,792 | 1/1994 | Leong et al. .............................. 600/515 |
| 5,312,443 | 5/1994 | Adams et al. . |
| 5,645,575 | 7/1997 | Stangl et al. .............................. 607/17 |

FOREIGN PATENT DOCUMENTS

| | | |
|---|---|---|
| 0 465 241 | 1/1992 | European Pat. Off. . |
| 0 653 224 | 5/1995 | European Pat. Off. . |

*Primary Examiner*—William E. Kamm
*Assistant Examiner*—Carl H. Layno
*Attorney, Agent, or Firm*—Hill & Simpson

[57] ABSTRACT

In a method for classifying IEGM waveforms in dependence of the workload of a patient, a predetermined number of IEGM-signals, each signal extending over at least one segment of one heart beat cycle, are registered, whereafter the IEGM-signals are fed to a neural network and an encoded form of the signals is formed using said neural network. This encoded form is stored in a memory, for use in classifying further registered IEGM-signals. In an active cardiac implant connectable to an implantable electrode arrangement adapted for in vivo delivery of stimulation pulses to a heart, IEGM signals present are obtained from one or more of the electrodes. A pulse generator connected to the electrode arrangement, generates and emits stimulation pulses with a variable stimulation interval between successive stimulation pulses. The implant also contains a classifying device for classification of a predetermined number of IEGM-signals registered during predetermined time intervals at predetermined points of time according to a predetermined classification stored in the classification device, this classification being related to preregistered waveforms of measured IEGM-signals. A control unit in the implant supplies a control signal to a control input of the pulse generator dependent on the classification of each of the registered IEGM signals. The control signal causes the pulse generator to adjust the stimulation rate dependent on each of the registered IEGM-signals.

13 Claims, 5 Drawing Sheets

RATE RESPONSIVE HEART STIMULATION DEVICE USING NEURAL NETWORK AND IEGM CLASSIFIER

FIELD OF THE INVENTION

The present invention relates to a rate-responsive pacemaker of the type having at least one pulse generator which generates and emits stimulation pulses with a variable stimulation interval, and a control device which controls the pulse generator's stimulation intervals, as well as to a method for rate-regulation of the stimulation pulses.

DESCRIPTION OF THE PRIOR ART

A disadvantage of most known pacemakers is a relative lack of a physiological rate control. A rather large group of physically active patients would benefit from improvements in this area. In addition to, for instance, impedance measurements, for relating oxygen demand of the patient to the workload, several other solutions have been tested but they still do not deliver accurate cardiac rate regulation. Other such methods include the use of sensors measuring different physical parameters such as acceleration or blood pressure. The use of sensors of different kinds of course complicates the heart stimulators, leading to increased manufacturing costs and reduced reliability since the possibility of component failure in any one of the components increases proportionally to the number of components.

SUMMARY OF THE INVENTION

An object of the invention is to provide a rate-responsive heart stimulator which effectively optimizes cardiac output on the basis of measurable activities in the heart, and a method for controlling the same.

Another object is to provide a method useable in a heart stimulator for relating these same measurable activities in the heart to the situation of the patient, i.e., the oxygen demand of the body of the patient.

When blood in the heart has been expelled in a normal cardiac cycle and the muscle tissue relaxes for refilling, the influx of blood into the heart is governed by blood pressure in the vascular system. At the beginning of diastole the blood flows-rapidly into the heart. The flow ultimately ceases when the heart is full of blood, i.e. when the pressure in the heart and in the vascular system equalize. In addition, the influx of blood into the heart depends on the physical and mental condition of the person in whom the stimulation device is implanted. At rest, the influx of blood into a patients's heart is slower at the beginning of diastole than during physical exercise or stress.

When a patient experiences a workload there is a need for extra oxygen, which need can be satisfied by, e.g., an increase in the heart rate such that the flow of blood through the heart increases. An other method is to increase the stroke volume. Both of these will invariably result in physiological changes in the heart muscle.

It has now surprisingly been found that when registering IEGMs (Intracardiac electrograms) systematic changes in the IEGM waveform morphology appear as to a patient. It has also surprisingly been found that these systematic changes in the IEGM can be used for estimating the workload of the specific patient experiences a workload. It has also surprisingly been found that these systematic changes in the IEGM can be used for estimating the current workload of the specific patient.

The present invention is based on the observation that when a constant stimulation rate is maintained and the level of physical exercise (i.e. oxygen demand of peripheral tissue) is varied, systematic changes in IEGM wave-form morphology occur.

It has now surprisingly been found that these waveform morphology changes can be used to rate regulate a heart-stimulator in a way which does not require the use of any additional intra- and/or extracardiac sensors or electrodes. Such extra devices invariably create an increased power demand for the implanted device, which means that the absence of such extra sensors or electrodes allows the desire for low power consumption to be more easily fulfilled than has been accomplished with known methods. Such extra electrodes and/or sensors may also cause electrical interference with the necessary registering of the heart activity. Thus it has been shown that according to the invention the morphology changes can be used to control a stimulator which does not make use of extra intracardiac or extra-cardiac sensors.

Accordingly, the above objects are achieved in an inventive method and apparatus for classifying IEGM waveforms dependent on a workload experienced by a patient producing the IEGM waveforms, wherein a predetermined number of IEGM signals are obtained from the patient, each IEGM signal having an IEGM waveform associated therewith extending over at least one segment of one heartbeat cycle of the patient, wherein the IEGM signals are supplied to a neural network which forms an encoded form of each IEGM waveform, wherein the encoded forms of the IEGM waveforms are stored in a memory, and wherein, for subsequently obtained IEGM signals, the previously-obtained IEGM waveforms stored in encoded form are used for classifying the respective waveforms of the subsequently-obtained IEGM signals, and thus the subsequently-obtained IEGM signals themselves are classified.

DESCRIPTION OF THE PREFERRED EMBODIMENTS

Figure 1:
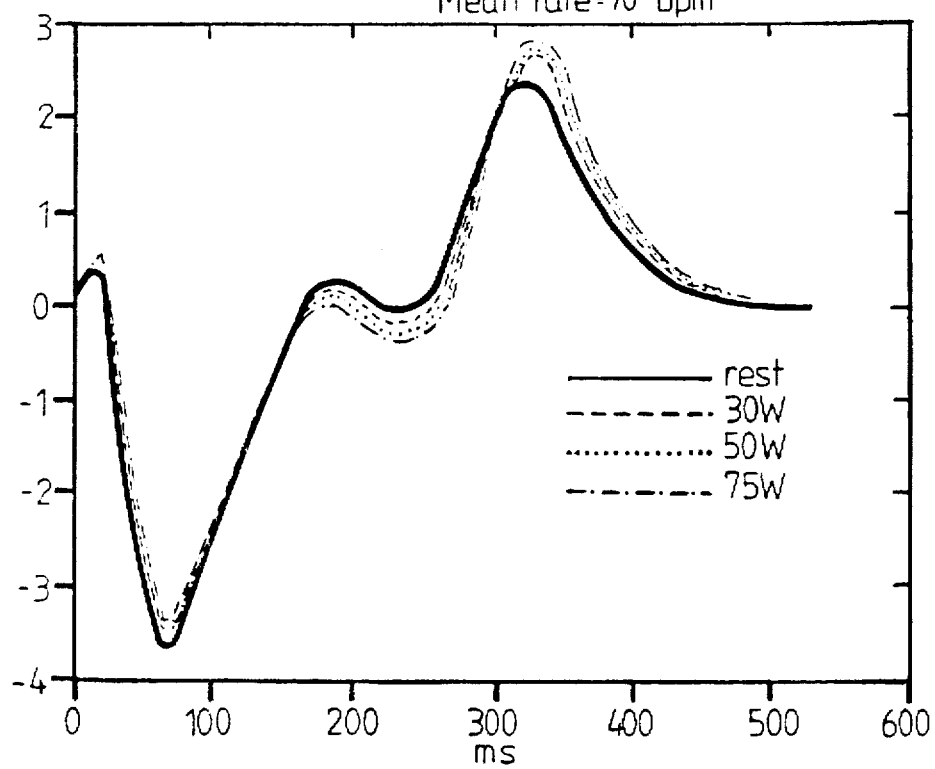
FIG. 1 is a diagram showing averaged IEGM measurements from a bipolar lead in the ventricle, the patient being put under different workloads and being paced with a mean (average) rate of 70 bpm.

FIG. 1 shows averaged IEGM measurements for different loads formed from 20 consecutive heart beats recorded from a bipolar lead. The lead was placed in the ventricle and both the sampling and the stimulation was performed via the same lead. The patient with a recently implanted pacemaker, was paced at 70 bpm throughout the recording of the IEGMs. The recording of the IEGMs was started at the stimulation pulse and the sampling rate was 100 samples/s making each sample correspond to 10 ms. The X-axis is in ms and the Y-axis corresponds to the polarity and amplitude of the sampled points. The curves in the diagram correspond to the different workloads applied rest, 30 watts (of expended power by the patient), 50 watts and 75 watts. The most interesting segments of the IEGMs occur between 175 ms to 425 ms after the time of the stimulation pulse.

The method according to the invention may use all of the registered IEGM, or segments of the IEGM may be chosen for use with the method according to the invention. This means that the measured IEGMs all must be related to a predetermined point of time, which in this case could be the stimulation pulse.

If in this case the patient had an active implant which would allow for the possibility of a spontaneous heartbeat and only would emit a stimulation pulse in the absence of a spontaneous beat, this stimulation pulse would then be the predetermined point of time for the actual measurement.

Figure 2:
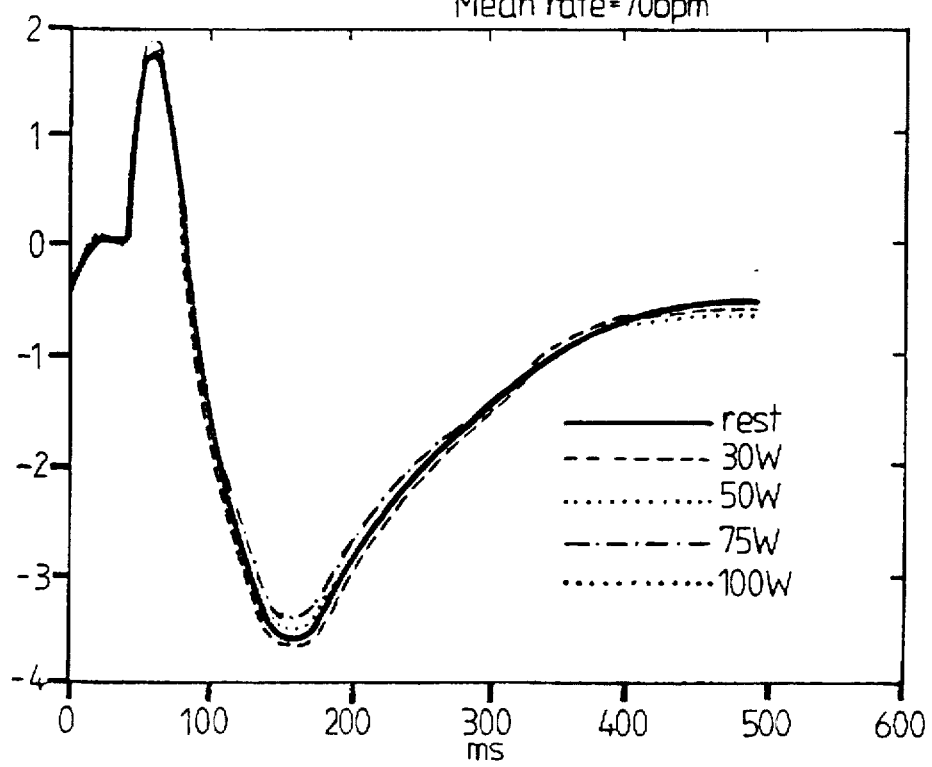
FIG. 2 is a diagram showing averaged IEGM measurements from a unipolar lead in the ventricle with the patient being paced at a rate of 70 bpm.

FIG. 2 shows averaged IEGM measurements for different loads formed over 20 consecutive heart beats recorded from a unipolar lead. The lead was placed in the ventricle and both the sampling and the stimulation was performed via the same lead. The patient, with a chronic implanted pacemaker, was paced at 70 bpm throughout the recording of the IEGMS. Chronic means that the electrodes and the leads have been implanted for some time as compared with acute. The sampling rate is 100 samples/s, making each sample correspond to 10 ms. The X-axis is graduated in ms and the Y-axis corresponds to the polarity and amplitude of the sampled points. The curves in the diagram correspond to the different workloads applied: rest, 30 watts, 50 watts, 75 watts and 100 watts. The most interesting segment seems to be about 100 ms to 300 ms from the stimulation pulse.

In the figures the total time window is 500 ms, which corresponds to 51 samples. At the paced rate of 70 bpm the time between each heart stroke is 860 ms. During the 360 ms not shown in the graphs in the figures the registered signal is essentially isoelectric (0 V) and thus not of interest for showing changes under different workloads.

As can be seen from the curve in FIG. 1 there are registerable changes between the curves related to different loads. is It is to be noted that IEGMs from different leads and different persons will always look different. In the same person the curve registered will also depend on the exact location of the tip of the lead. There is of course a relation to the appearance of the surface-ECG but the appearance of the IEGM is different because the signals are directly measured in the heart itself and not on the surface of the body.

The same type of changes can be seen in the graph in FIG. 2 where the most important changes in amplitude seem to occur in the area around 150 to 260 ms. The type of lead and the exact location of the electrodes of the lead accounts for the general appearance of the IEGM registered. This is purely a methodology question depending on how the leads are connected when measuring.

Thus it can be concluded that the area where the changes in the waveform are most prominent corresponds to the latter part of the QRS-complex and the T-wave.

According to the present invention it has been shown that these noted changes may be used as the qualitative basis for the rate-responsive heart stimulation. The differences in between the different load cases are not very large, but are still quite easily detected by using a form of a neural network.

The principle employed in the inventive method and apparatus is to provide a device able to classify registered IEGMs as waveforms, i.e. the registered IEGMs such as shown in FIG. 1 and FIG. 2 above. These classified waveforms are then entered into a wavetable.

A wavetable, (waveform table) is an organized storage of waveforms. The origin of the term comes from sound synthesis technology where digitized waveforms are stored in a memory as a wavetable. The waveforms according to the present invention are not easily retrievable since their characteristics are coded in the synaptic weights of a neural network, however, the abstract concept of a wavetable is useful for explaining the present invention.

The classification of the registered waveforms is accomplished using e.g. a neural network. In order to do this it is preferred that the individual patient perform a series of workloads e.g. on an ergometric cycle. For each workload a range of pacing rates are scanned, i.e. the patient goes through a number of tests under the same load but with the pacing rate set differently for each run. For each rate the waveform is recorded by the device. A wavetable may be stored relating pacing rate and workload and morphology for the specific patient.

Figure 4:
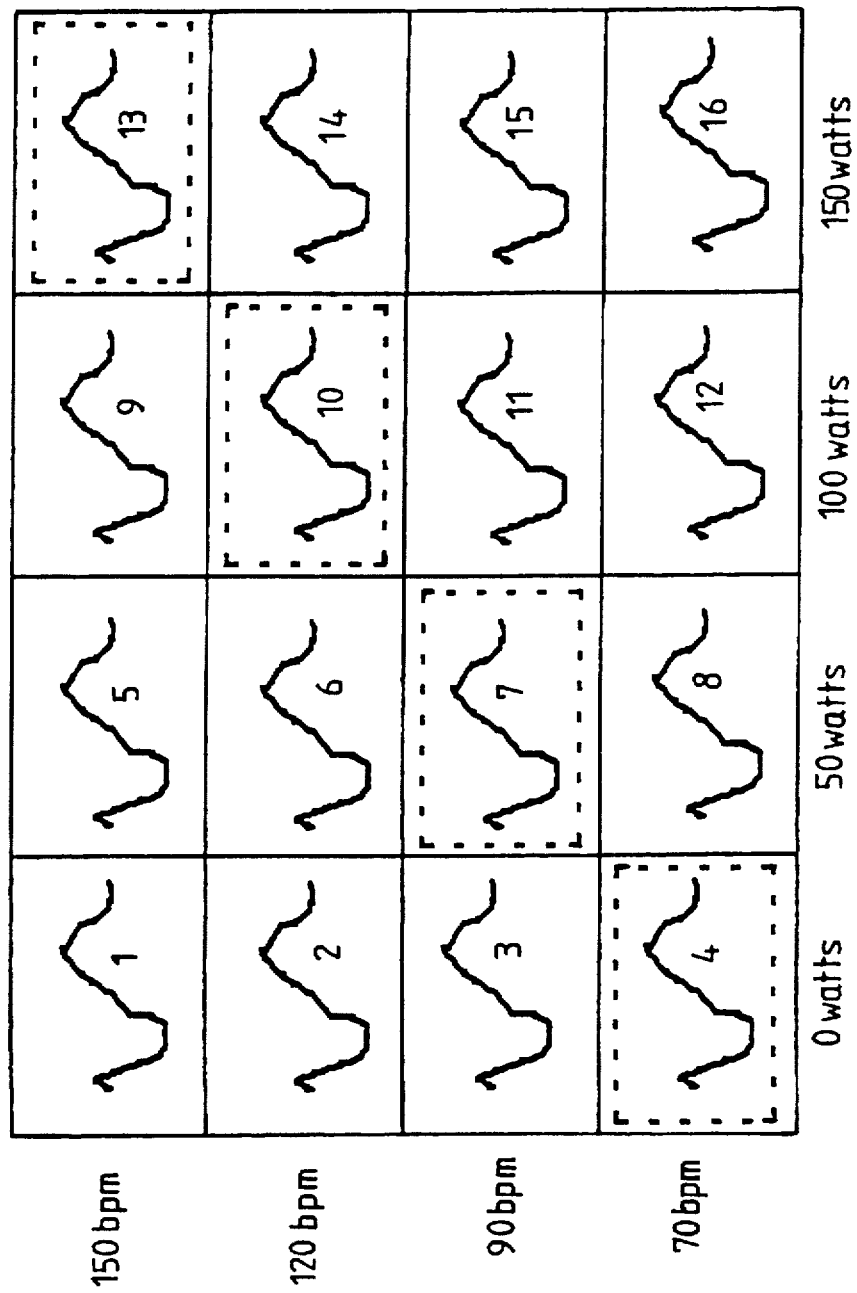
FIG. 4 shows an example of a wavetable in accordance with the invention.

Such a wavetable is shown in FIG. 4. In the table waveforms corresponding to different heart rates and different workloads for a patient are shown and the waveform presenting the most favorable pacing rate for the actual workload is marked by a dashed box. Thus it may be inferred from this wavetable that at rest the patient preferably should be under a stimulation rate of 70 bpm and when under a workload of 100 watts should preferably be under a stimulation rate of 120 bpm.

In order to realize these waveform patterns, a neural network may be utilized. Such a device has to undergo a training procedure to be able to recognize and categorize different waveforms.

The neural network is applied for performing a classification of the waveforms, as a part of the monitoring of the pacing, during the use of the heart stimulator. In one instance 51 consecutive samples have been used as an input series to the neural network for training a multilayer perception with back-propagation. The recorded IEGMs were digitized and stored in a computer, then an IEGM morphology analysis and the neural network simulations were made. Using this relatively crude method correct classifications could be made on a beat to beat basis.

Since the IEGM waveform changes with pacing rate, the neural network has to be trained with segments of waveform data from a number of heartbeat intervals from the patient and also several different pacing rates. The network may, e.g., be trained on data from a chosen number of corresponding segments and heart rates, the segments preferably being those segments showing the biggest variations between different workloads.

Training the neural network is computationally extensive and may therefore be performed in a separate external unit, where power consumption is not a problem. The parameters of the trained network are then transferred to the pacemaker, which only performs the classification. Since classification requires relatively few operations it can be performed in an implantable device with low power consumption.

Figure 3:
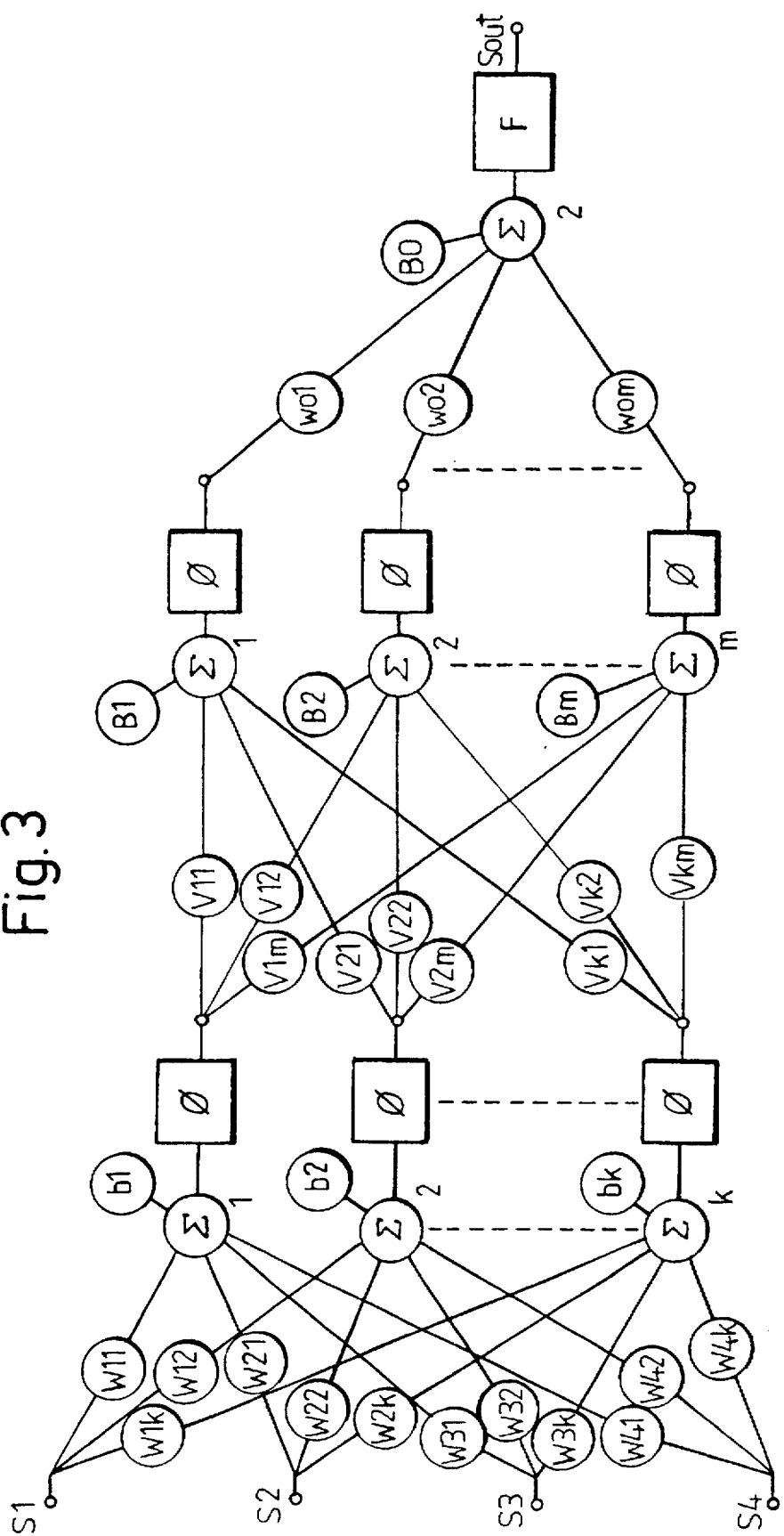
FIG. 3 is a schematic drawing of one possible implementation of a neural network or signal processing system for use in the inventive method and apparatus.

In this context a short description of a neural network, a multilayer feed forward network, is presented in connection with FIG. 3.

The use of neural networks for detection and classification of intracardiac electrograms primarily for detecting arrhythmias are known from European Application 0 465 241 and U.S. Pat. No. 5,280,792.

A neural network generally has the option of receiving several input signals and generating therefrom one or more output signals. Each input signal is processed and combined with the other weighted input signals. The combinations of the signals are further processed in order to produce one or more output signals. The processing of the signals includes multiplication, addition and non-linear operations. A neural network may have different structures. This structure must first be decided. The neural network then has a number of hidden parameters ($W_{nn}$, $b_n$, weights and biases). A characteristic for the neural network is that it must learn how to adjust these parameters.

The input signals shown are in the shown example are S1, S2, S3 and S4. Each input signal is then multiplied by a certain weight ($W_{11}$ to $W_{4k}$). For every input signal there are as many weights as there are summing junctions. In FIG. 3 there are k summing junctions. In a summing junction all weighted signals and a bias signal are added. The bias signal is a constant necessary for the functioning of the neural network.

The output signal from the summing junctions is then passed through a transfer function, denoted "φ". Very often this transfer function is a non-linear function, like the sigmoid function. In the very same way as the input signals are processed, the output signals from the transfer function blocks are now handled. Here there are new weights and biases, $v_{11}$ to $V_{km}$ $b_1$ to $b_{m*}$. In FIG. 3 only one single output Sout is shown. The transfer function is denoted "F". Normally this last transfer function is a linear function.

The neural network used in the method according to the invention can be somewhat different from the above example but the operation of the network will be the same.

The learning action is performed on representative input signals which are fed into the neural network in order to produce an output signal or pattern, which will be compared with a reference signal or pattern. The learning procedure is performed by repeatedly feeding these input signals to the neural network and adjusting each parameter so that finally the output signal or pattern from the neural network resembles the reference signal or pattern. The neural network is now adjusted. New input signals will then produce output signals or patterns, which will be similar to the signals or pattern that the process, which the neural network is simulating, will produce.

Neural networks are today relatively well established tools for pattern classification tasks. Several different network types and learning algorithms may be used for solving this particular problem. The invention has been tested with a multilayer feed forward network trained by using the back-propagation algorithm. There are also statistical methods equivalent to neural networks that do basically the same job. These methods, however, may be viewed as distinctly different from neural networks. Finally, a neural network can be converted to fuzzy logic so as to operate as a fuzzy logic processor. Fuzzy logic may be more favorable than neural networks for hardware implementation.

When the pacemaker is in use the device continuously monitors the heart beats. This includes monitoring of the waveforms. If the waveform detected by the device is not optimal, the pacing rate has to be changed either upwardly or downwardly, depending on the characteristics of the waveform. This procedure will be repeated until the device finds an optimal waveform match.

The waveform table (wavetable) after being produced is stored in the implantable device and may be fine-tuned by the patient or by a doctor.

Figure 5:
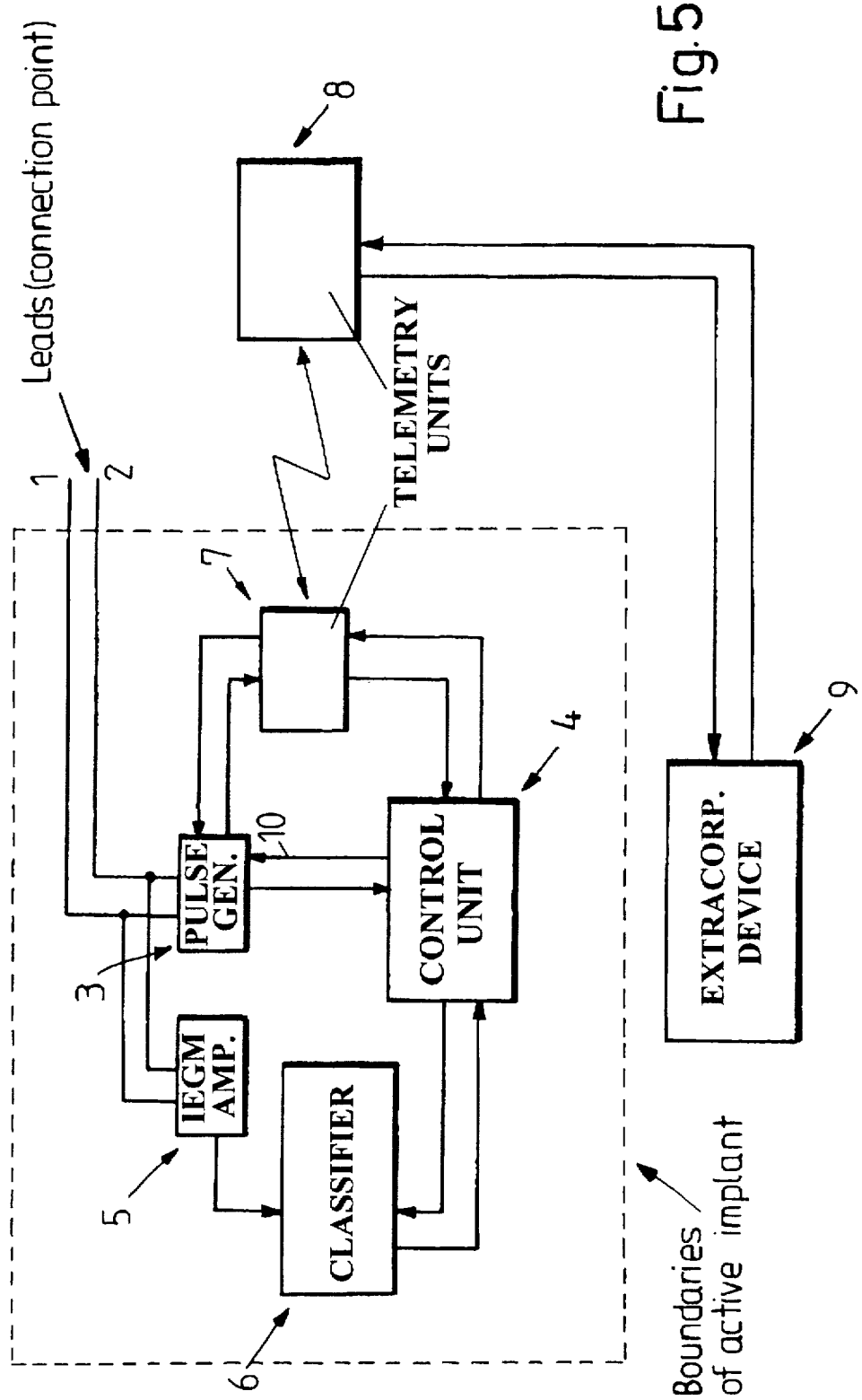
FIG. 5 is a schematic block diagram of an embodiment of an implantable heart stimulator according to the invention.

FIG. 5 shows an embodiment of the device according to the invention in the form of an active implant. The units within the dashed line are units contained within the implant, in a housing having a size and shape adapted for implantation in a patient. Connected to the input terminals 1 and 2 of a unipolar or bipolar lead is a pulse generator 3, shown as a functional block. This block contains circuitry for generating the, heart stimulation pulses. The block also contains circuitry for interfacing with the control unit 4. The control unit 4 has a overriding function in establishing the stimulation rate.

In another embodiment the control functions could just as well be placed in another unit, since this is only a matter of organizing the functions.

The device also includes an IEGM amplifier 5 for amplification and filtering of the IEGM signal The amplifier 5 is connected to the input terminals for receiving IEGM signals from connectable implanted leads and for amplifying the IEGM signals. The amplified signal are thereafter sent to the next block in the implantable device.

The next block is a classifier 6. Its main function is to classify the registered IEGMs into different morphological groups (wave groups). This is essential to the described rate regulation method. The classifying function can be implemented in several different ways, both with regard to the underlying algorithms and the hardware used, as will be discussed below in connection with FIGS. 6 and 7.

The control unit 4 interprets classification results from the classifier 6 and based thereon sends rate regulating signals to a control input 10 of the pulse generator 3.

The control unit 4 also controls which set of weights is to be used by the classifier 6 and handles the transfer of weights via telemetry. The wave table is coded as several sets of weights.

The active implant also has a telemetry unit 7 that allows for bidirectional transfer of data.

An external telemetry unit 8 is also shown, which is connected to an extracorporeal device 9 in which the training process of the neural network may be performed. The device 9 receives IEGM data from the active implant and trains an external neural network using that data and sends the weights, which constitute the underlying data for the wave table, back to the implant, to be used by the classifier 6 in conjunction with the control unit 4 in regulating the stimulation rate so as to be appropriate one the situation, i.e., for the workload to which the patient is subjected.

In the future an external unit for training of the neural network may not be necessary in implementations of the active implant according to the invention since the power consumption for sending bulk data via telemetry soon may be balanced by the power used for training carried out in the active implant.

The once established weights may for different reasons have to be changed by training the network all certain intervals, i.e., in case of major changes in the status of the patient's heart. These changes must not necessarily be dependent on serious events occurring in the heart. Also due to the natural ageing of the heart one might suspect that the waveform table once registered may have to be changed. This means that a new set of weights should be established as functions of different workloads and rates. The correlation between workloads and the preferred pacing rate for the specific workload may have been changed.

This will be rather simple, however, since new IEGMs may be registered using the already implanted leads and the signals may then be sent via the telemetry units to the extracorporeal device for establishing new classifier parameters.

Below follows a description of the tuning of the pacemaker to the individual patient.

After implantation of the device the patient performs a workload test on an ergometric cycle or a treadmill. At this stage the device will register IEGM-signals similar to those shown in FIGS. 1 and 2. At each workload level several stimulation rates are used and IEGMs for a predetermined number of heart cycles are recorded for each heart rate and workload. The patient and/or the physician will decide on a stimulation rate as optimal for each level of exercise. In this way the wavetable (FIG. 4) is established.

The IEGM waveforms are sent via telemetry to the external device 9. The external device 9 will use the data for training a neural network identical to the one used in the classifier 6. Some of the data will be used for validation of the network function.

Once the neural network in the external device 9 performs satisfactorily the internal weights will be sent back via telemetry to the weight memory of the classifier 6.

During normal operation the implanted device continuously analyses the IEGM waveform morphology and controls the heart stimulation rate thereafter.

Below is an example of the normal behavior of the active implant in use, which will be described using FIG. 4 as an example.

1. The patient is resting and the stimulation rate is 70 bpm, the IEGM waveform will have the appearance of #4. Since this is an optimal waveform no action is taken.

2. The patient starts to walk and the rate remains 70 bpm. The output of the classifier 6 will indicate waveform #8, which is not optimal. In order to retain the optimal waveform the control unit will step up the rate to 90 bpm where waveform #7 will be indicated. Since #7 is an optimal waveform no further action is taken.

3. The patient goes back to rest but the rate remains 90 bpm. Waveform #3 will be indicated by the classifier. #3 is not an optimal waveform and the rate will be decreased by the control unit to 70 bpm.

The following is an example of the procedural set-up. IEGMs were recorded via temporary transcutaneous leads, connected to the implanted pacemaker system. The transcutaneous leads were attached to the pacemaker connector. After the experiment the temporary leads were disconnected by pulling them out. Both acute and chronic transveneous leads were used. All experiments were performed one day after the new implantation or replacement of the pacemaker. The experimental protocol consisted of a series of workload tests, typically at 30 to 75 wafts. The recorded IEGMs were digitized and stored in a computer. The IEGM morphology analysis and the neural network simulations were made by using MATLAB® from MathWorks Inc.

A multilayer perception trained with back-propagation is used. The neural network was trained on data from 20 segments of the IEGMs at each workload level. The workload related morphological changes occurred mainly in the part of the IEGM corresponding to the ST-segment of a surface-ECG.

Two examples of implementations of the neural network (classifier 6) are given below.

Figure 6:
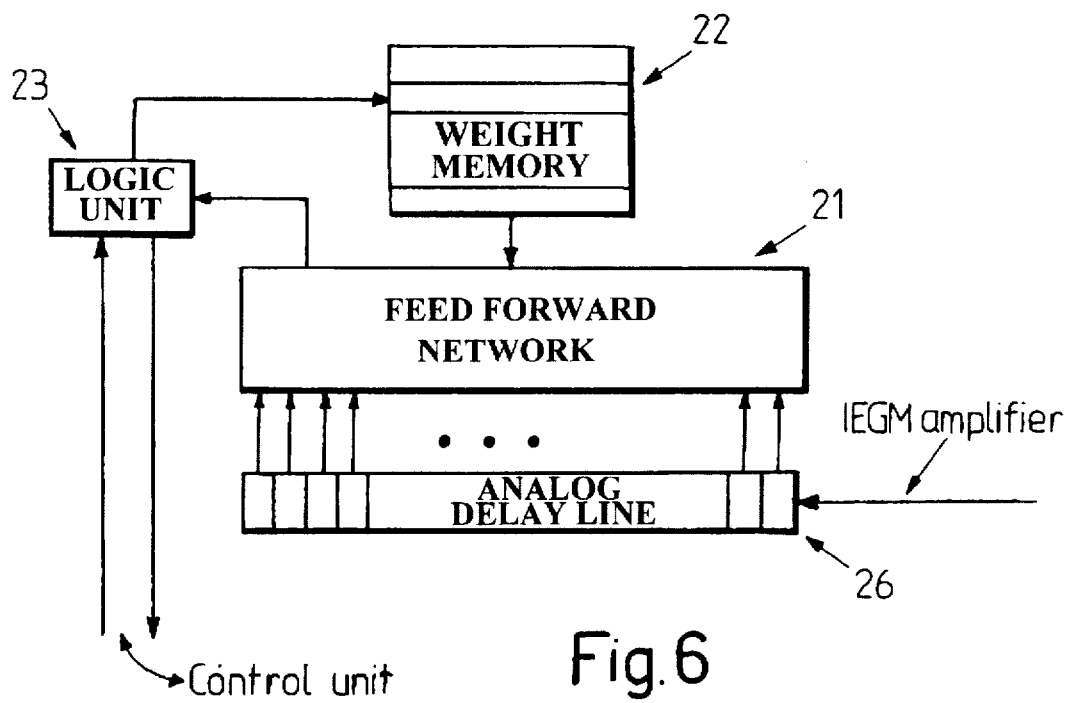
FIG. 6 shows an example of a neural chip-based classifier for use in the inventive method and apparatus.

In FIG. 6 an embodiment of the classifier, which is part of the active implant in the form of a neural chip is schematically shown. The measured analog IEGM signal coming on line 1 from the IEGM amplifier (not shown) in the active implant is fed into a analog delay line 26, with each segment of the delay line being connected via a conductor to a corresponding input of a feed forward network 21. The input signal is classified and the result of the classification is sent via conductor 3 to the logic unit 23 that passes it on via conductor 5 to the control unit (not shown) of the active implant (FIG. 1). The weights of the network are stored in the weight memory 22, which has sufficient capacity for the storage of several sets of weights. The logic unit 23, connected to the control unit (not shown) and to the weight memory 22 selects which set of weights to use. The logic unit 23 receives information via a conductor 6 as to which set of weights to use from the control unit (not shown) of the active implant. The control unit bases its decision on the current heart stimulation rate forwarded from the pulse generator (not shown).

Figure 7:
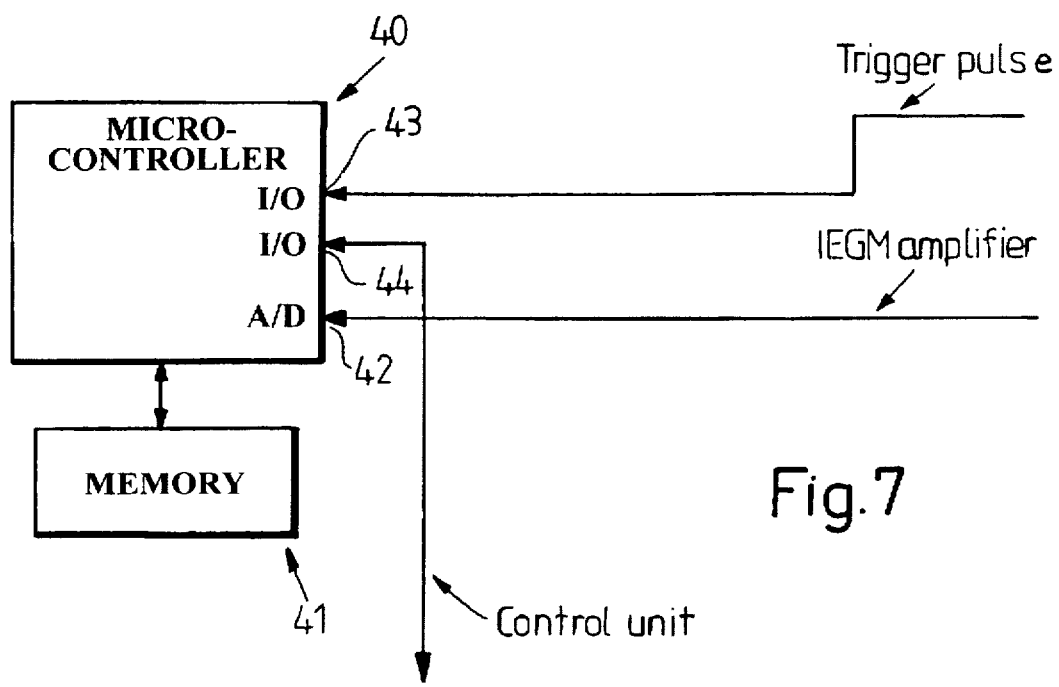
FIG. 7 shows an example of a microcontroller based classifier implementation for use in the inventive method and apparatus.

In FIG. 7 an embodiment of the classifier based on a microcontroller is shown. The analog in-IEGM signal is fed into an A/D port 42 of the microcontroller 40. The microcontroller 40 interacts with a memory 41 for weight and data storage, which may be an integral part of the microcontroller 40. The microcontroller receives trigger pulses from the pulse generator (not shown) via a digital input/output port 43. Via another digital input/output port 44 the microcontroller 40 has a bidirectional communication with the controller unit (not shown) of the active implant.

The microcontroller has a neural network simulation program. The training is analogous with the earlier described method using an external computer. The segments of the registered IEGMs of interest in the individual patient is chosen and in the classifying procedure the choice of segments of the registered signals are synchronized using, e.g., the stimulation pulse or some other well-defined event in the heart beat cycle. The software running the microcontroller may be set up to form an average of 5 or 10 waveforms and classify the average waveform as belonging to a certain group.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for setting a cardiac stimulation rate dependent on a workload experienced by a patient, comprising the steps of:

obtaining a predetermined number of IEGM signals from a patient respectively while said patient is subjected to different workloads, each IEGM signal having an IEGM waveform associated therewith extending over at least one segment of one heartbeat cycle of said patient;

supplying said IEGM signals to a neural network and forming an encoded form of said IEGM waveforms using said neural network;

storing said encoded form of said IEGM waveforms in a memory;

obtaining subsequent IEGM signals, each subsequent signal having an IEGM waveform associated therewith, and using said IEGM waveforms in encoded form stored in said memory for classifying the respective waveforms of said subsequent IEGM signals to identify a current workload of said patient; and administering pacing stimulation pulses to said patient at a stimulation rate matched to said current workload of said patient.

2. A method as claimed in claim 1 wherein the step of obtaining said IEGM signals comprises, for each workload, pacing said patient at a plurality of different stimulation rates and obtaining an IEGM signal with an IEGM waveform for each stimulation rate for each workload so that each stimulation rate for each workload has an IEGM waveform associated therewith, which is subsequently formed in encoded from by said neural network, and storing said stimulation rates respectively correlated with their associated IEGM waveforms in encoded form.

3. A method as claimed in claim 2 comprising the additional step of supplying stimulation pulses at a current stimulation rate to said patient while obtaining said subsequent IEGM signals, and wherein the step of using IEGM waveforms for classifying comprises, for each subsequent IEGM signal, classifying said subsequent IEGM signal by matching its IEGM waveform to one of the stored IEGM waveforms and identifying the stimulation rate associated with said one of said stored waveforms, and said method comprising the additional step of changing said current stimulation rate to the stimulation rate associated with said one of said stored IEGM waveforms if said current stimulation rate is different from said stimulation rate associated with said one of said stored IEGM waveforms.

4. A method as claimed in claim 1 wherein the step of forming an encoded form of said IEGM waveforms using said neural network comprises selecting at least one segment of said heartbeat cycle represented by an IEGM signal and using said at least one segment for forming said encoded form of the IEGM waveform associated with that IEGM signal.

5. A method as claimed in claim 1 wherein the step of forming an encoded form of said IEGM waveforms using said neural network comprises obtaining an average of a plurality of said at least one segment of each heartbeat cycle over a plurality of heartbeat cycles respectively represented by IEGM signals and using said average for forming said encoded form of the IEGM waveforms respectively associated with those IEGM signals.

6. A method as claimed in claim 1 wherein the step of forming an encoded form of said IEGM waveforms using said neural network comprises obtaining an average of a plurality of heartbeat cycles respectively represented by IEGM signals and using said average for forming said encoded form of the IEGM waveforms respectively associated with those IEGM signals.

7. A method as claimed in claim 1 wherein the step of obtaining a plurality of IEGM signals comprises obtaining a plurality of IEGM signals respectively from a plurality of consecutive heartbeat cycles.

8. A cardiac assist system for pacing a heart of a patient dependent on a current workload experienced by said patient, said system comprising:

a housing having a size and shape adapted for implantation in a patient;

pulse generator means, disposed in said housing, for generating and emitting stimulation pulses with a variable stimulation interval between successive stimulation pulses, said pulse generator means having an output at which said stimulation pulses are present, and a control input;

electrode means, connectable to said output of said pulse generator means, for delivering said stimulation pulses in vivo to the heart of said patient;

monitoring means, contained in said housing and connected to said electrode means, for registering IEGM signals associated with said heart at different workloads and different stimulation intervals, each IEGM signal having an IEGM waveform associated therewith;

memory means in said housing for storing a plurality of IEGM waveforms respectively associated with said IEGM signals at said different workloads and different stimulation intervals;

classifier means, having access to said memory means and supplied with subsequent IEGM signals from said monitoring means, respectively obtained at predetermined points in time during a predetermined time interval, for classifying a predetermined number of said subsequent IEGM signals by classifying the IEGM waveforms respectively associated with said subsequent IEGM signals as matching an IEGM waveform in said memory means; and control means, contained in said housing and connected to said classifier means, for generating a control signal dependent on the classification of said subsequent IEGM signals and for supplying said control signal to said control input of said pulse generator means for varying the stimulation interval dependent on the workload associated with the subsequent IEGM signals.

9. A cardiac assist system as claimed in claim 8 wherein said classifier means comprises a neural network, contained in said housing, and supplied with at least one segment of one heartbeat cycle for each IEGM signal, said neural network forming an encoded form of the IEGM waveform associated with said at least one segment of each IEGM signal, and wherein said memory means comprises means for storing said encoded form of each IEGM waveform.

10. A cardiac assist system as claimed in claim 8 wherein said classifier means comprises a neural network disposed externally of said housing, said neural network being supplied with a predetermined number of said IEGM signals, each IEGM signal extending over at least one segment of one heartbeat cycle, said neural network forming encoded forms of the respective IEGM waveforms associated with each IEGM signal, and said system further comprising telemetry means for telemetrically transmitting said predetermined number of IEGM signals from said housing to said neural network and for telemetrically receiving said IEGM signals in encoded form and for supplying said IEGM signals in encoded form, upon receipt thereof, to said memory means for storage therein.

11. A cardiac assist system as claimed in claim 8 wherein said classifier means comprises a fuzzy logic processor disposed externally of said housing, said fuzzy logic processor being supplied with a predetermined number of said IEGM signals, each IEGM signal extending over at least one segment of one heartbeat cycle, said fuzzy logic processor forming encoded forms of the respective IEGM waveforms associated with each IEGM signal, and said system further comprising telemetry means for telemetrically transmitting said predetermined number of IEGM signals from said housing to said fuzzy logic processor and for telemetrically receiving said IEGM signals in encoded form and for supplying said IEGM signals in encoded form, upon receipt thereof, to said memory means for storage therein.

12. A cardiac assist system as claimed in claim 8 wherein said memory means comprises means for storing a plurality of IEGM waveforms respectively obtained while pacing said patient at a plurality of different stimulation rates so that each stimulation rate for each workload has an IEGM waveform associated therewith with said stimulation rates respectively correlated in said memory means with their associated IEGM waveforms, and wherein said classifier means comprises means for classifying said current IEGM signal by matching its IEGM waveform to one of the stored IEGM waveforms and identifying the stimulation rate associated with said one of said stored waveforms, and wherein said control means comprises means for changing said stimulation interval to a stimulation interval associated with the stimulation rate of said one of said stored IEGM waveforms if said current stimulation rate is different from the stimulation rate associated with said one of said stored IEGM waveforms.

13. A cardiac assist system as claimed in claim 8 wherein said classifier means comprises means for classifying respective segments of the IEGM signal for each heartbeat cycle occurring between 175 ms and 425 ms after generation of a stimulation pulse by said pulse generator means.

* * * * *